United States Patent
Melsheimer (10) Patent No.: US 9,108,032 B2
(45) Date of Patent: Aug. 18, 2015

(54) HEMOSTASIS VALVE ASSEMBLY

(75) Inventor: Jeffry S. Melsheimer, Springville, IN (US)

(73) Assignee: COOK MEDICAL TECHNOLOGIES LLC, Bloomington (IN)

( * ) Notice: Subject to any disclaimer, the term of this patent is extended or adjusted under 35 U.S.C. 154(b) by 904 days.

(21) Appl. No.: 13/203,303

(22) PCT Filed: Mar. 2, 2010

(86) PCT No.: PCT/US2010/025836
§ 371 (c)(1),
(2), (4) Date: Oct. 25, 2011

(87) PCT Pub. No.: WO2010/104694
PCT Pub. Date: Sep. 16, 2010

(65) Prior Publication Data
US 2012/0065474 A1    Mar. 15, 2012

Related U.S. Application Data

(60) Provisional application No. 61/159,490, filed on Mar. 12, 2009.

(51) Int. Cl.
*A61B 1/267* (2006.01)
*A61M 39/06* (2006.01)

(52) U.S. Cl.
CPC ........... *A61M 39/06* (2013.01); *A61M 39/0606* (2013.01)

(58) Field of Classification Search
CPC ........... A61B 17/3421; A61B 17/3462; A61B 17/3439; A61B 17/3498; A61B 2017/3492; A61B 2017/3419; A61B 2017/3441
USPC ................... 606/185; 600/208; 604/167, 171
See application file for complete search history.

(56) References Cited

U.S. PATENT DOCUMENTS

| 4,430,081 A | | 2/1984 | Timmermans ................ 604/256 |
| 5,006,113 A | | 4/1991 | Fischer ......................... 604/167 |
| 5,350,364 A | * | 9/1994 | Stephens et al. ......... 604/167.06 |
| 5,397,314 A | * | 3/1995 | Farley et al. ................... 604/256 |

(Continued)

FOREIGN PATENT DOCUMENTS

| EP | 1637178 A1 | 3/2006 | ............ A61B 17/34 |
| WO | WO 2005/058409 A1 | 6/2005 | ............ A61M 39/06 |
| WO | WO 2008/017254 A1 | 2/2008 | ............ A61B 17/94 |

*Primary Examiner* — Jerry Cumberledge
*Assistant Examiner* — Tessa Matthews
(74) *Attorney, Agent, or Firm* — Brinks Gilson & Lione (57) ABSTRACT

A valve assembly (10) for controlling a flow of fluid includes a housing (30) having a passageway (33), and a valve sheath (40) disposed interiorly of the housing, at least substantially along the housing passageway. The valve sheath includes a cylindrical valve body (42) having a pair of generally wedge-shaped voids (50A, 52A) formed along opposing longitudinal sides of the valve body. Each of the wedge-shaped voids comprises first and second inwardly-directed sides that converge to define a generally linear edge. The edges are disposed along the valve body in a generally diagonal orientation with respect to a longitudinal axis through the valve body. The respective linear edges are structured and aligned in the valve body to meet along a passageway through the valve body interior in a manner to selectively close the valve body interior passageway, and to yield to permit passage of an interventional device therethrough.

14 Claims, 6 Drawing Sheets

(56) References Cited

U.S. PATENT DOCUMENTS

| | | | |
|---|---|---|---|
| 5,916,198 A * | 6/1999 | Dillow | 604/167.04 |
| 6,416,499 B2 | 7/2002 | Paul, Jr. | 604/256 |
| 7,172,580 B2 * | 2/2007 | Hruska et al. | 604/248 |
| 8,016,797 B2 * | 9/2011 | Gratwohl et al. | 604/192 |
| 2008/0157017 A1 | 7/2008 | Macatangay et al. | 251/314 |
| 2011/0152626 A1 * | 6/2011 | Smith | 600/208 |
| 2011/0295076 A1 * | 12/2011 | Smith | 600/208 |
| 2012/0172668 A1 * | 7/2012 | Kerns et al. | 600/208 |

* cited by examiner

HEMOSTASIS VALVE ASSEMBLY

BACKGROUND

1. Technical Field

The present invention relates to a valve assembly. More particularly, the invention relates to a hemostasis valve assembly for use with a medical device, such as an introducer sheath, to permit substantially leak-free passage therethrough of an interventional device for insertion into a body vessel.

2. Background Information

A variety of well-known medical procedures are performed by introducing an interventional device, such as a catheter, trocar, sheath, stent and the like, into a vessel in a patient's body. Typical procedures for introducing an interventional device into a blood vessel include the well-known Seldinger technique. The Seldinger technique involves opening a blood vessel with a needle, inserting a wire guide into the vessel through the lumen of the needle, withdrawing the needle and inserting a dilator over the wire guide. The dilator is typically located inside an introducer sheath which is also inserted into the vessel, and the dilator is sealed to the sheath by a hemostasis valve through which the dilator passes. The dilator is thereafter removed, and an interventional device is inserted through the sheath and hemostasis valve into the vessel.

As the Seldinger technique and/or other interventional procedures are carried out, care must be taken to avoid the undesirable introduction or leakage of air into the vessel (air embolism), as well as the undesirable leakage of blood, other bodily fluids or cavity-pressurizing gas from the patient. As procedures for introducing catheters and other interventional devices have become more widely accepted, these procedures have become more diverse, and the variety of sizes and types of interventional devices has grown dramatically. As a result, the risk of inward or outward leakage of fluids has increased.

One known way to minimize such leakage is to provide one or more disk-like gaskets (often referred to as check valves) in an elongated passageway of a device through which fluids may pass into or out of the body. Such devices are generally positioned in a housing at a proximal end portion of the introducer, between a main body portion and an end cap. Each disk typically includes one or more slits, apertures, or other configurations extending at least partially through the disk to provide a sealable path to permit insertion of the medical interventional device through the disk, and to substantially prevent the backflow of fluids. Examples of such disks are provided in, among others, U.S. Pat. Nos. 4,430,081, 5,006,113 and 6,416,499, incorporated by reference herein. Such valves are now well known in the medical arts, and additional discussion of their use and function is not necessary for an understanding of the present invention.

Frequently, it is necessary to replace a previously-inserted medical interventional device with another interventional device of a different diameter, or with a different type of device. Such exchanges are often made over a wire guide, wherein the old device is withdrawn over the wire guide, and the new device is thereafter inserted into the body vessel over the existing wire guide or a newly-inserted wire guide. In many such cases, check valves are provided in an attempt to minimize leakage of blood back through the introducer. Such valves are dependent upon the elasticity of the valve body, and its ability to draw back upon itself to seal any gap created upon insertion or withdrawal of a device through the valve.

Known slitted check valves generally include one or more slits that criss-cross and span a center portion of the valve disk, or a hole disposed through the center of the disk. As the interventional device is passed through the center of a slit valve disk, the slits open outwardly and form one or more generally "V"-shaped openings that are disposed along the outer surface of the interventional device. Such linear-type openings often do not form tight seals, and inherently create gaps that permit the leakage of at least some fluid. As a result, these valve systems may comprise two or three such valve sheaths that are aligned in the valve housing in a manner such that the slit portions are not in axial alignment. Although this arrangement may reduce the amount of leakage when compared to the use of a single valve sheath, the presence of the gaps provides a conduit from which some leakage may occur. Similarly, the various flaps resulting from the slits do not always re-set in the proper manner following passage of the interventional device, thereby creating additional gaps through which fluid may leak.

Small size interventional devices are often delicate, and possess little hoop strength. When such devices pass through a check valve sheath, the thickness and strength of the valve sheath may cause damage to the delicate structure of the interventional device. In this case, the clearance between the opening in the disk and the interventional device can be so slight that it may be difficult to insert and/or withdraw the interventional device. In addition, on some occasions, additional small diameter tubing must be used to keep the valve open so that a catheter or other device may be passed therethrough. When additional equipment is required, such as a small diameter tube or a Tuohy-Borst valve, the surgeon's hands, and attention, may be unduly distracted at the very time when primary focus is most preferably directed to the task at hand.

When one or more valve disks having a hole through the center of the disk are used, the disks will only recover back to the size of the center hole following removal of the catheter. As a result, the respective center holes allow leakage once the catheter is removed. Such valves may be satisfactory when there is no need to remove the catheter that seals the opening; however, they can be problematic when the catheter is removed and the center opening is left unoccluded.

It is desired to provide a hemostasis valve assembly for a medical device that provides an effective seal, and that avoids the problems encountered with prior art seals.

SUMMARY

The present invention addresses the shortcomings in the prior art. In one form thereof, the invention comprises a valve assembly for controlling a flow of fluid. The valve assembly comprises a cannula body and a housing, each having a proximal end and a distal end. The housing distal end is engaged with the cannula body proximal end in a manner such that a passageway is defined therethrough for passage of an interventional device. A valve sheath is disposed at least substantially interiorly of the housing along the passageway. The valve sheath comprises a generally cylindrical valve body having an interior passageway therein for passage of the interventional device, and has a pair of elongated voids formed along opposing longitudinal sides of the valve body. The voids are configured such that a generally linear extension is defined along the valve body at an inward terminus of each of the voids. The respective generally linear extensions are structured and aligned in the valve body to meet along the interior passageway of the valve body in a manner to selectively close the interior passageway, and to yield to permit passage therethrough of the interventional device.

In another form thereof, the invention comprises a valve for use in controlling a flow of fluid. The valve includes a housing having a proximal end, a distal end, and a passageway extending therethrough. A valve sheath is disposed interiorly of the housing, at least substantially along the housing passageway. The valve sheath comprises a generally cylindrical valve body having a proximal end, a distal end, and a passageway therein. The valve body comprises a pair of generally wedge-shaped voids formed along opposing longitudinal sides of the valve body. Each of the generally wedge-shaped voids comprises first and second inwardly-directed sides that converge to define a generally linear edge. Each of the edges is disposed in a generally diagonal fashion to a longitudinal axis through the valve body. The respective linear edges are structured and aligned in the valve body to meet along the valve body passageway in a manner to selectively close the valve sheath interior passageway, and to yield to permit passage of an interventional device therethrough.

DETAILED DESCRIPTION OF THE DRAWINGS AND THE PRESENTLY PREFERRED EMBODIMENTS

For purposes of promoting an understanding of the present invention, reference will now be made to the embodiments illustrated in the drawings, and specific language will be used to describe the same. It should nevertheless be understood that no limitation of the scope of the invention is thereby intended, such alterations and further modifications in the illustrated apparatus, and such further applications of the principles of the invention as illustrated therein being contemplated as would normally occur to one skilled in the art to which the invention relates.

The present invention relates to a hemostasis valve assembly. The hemostasis valve assembly is primarily intended for use in combination with a medical device, such as an introducer sheath. In the following discussion, the terms "proximal" and "distal" will be used to describe the opposing axial ends of the hemostasis valve assembly, as well as the axial ends of other components of the assembly. The term "proximal" is used in its conventional sense to refer to the end of the hemostasis valve assembly (or component thereof) that is closer to the operator during use of the device. The term "distal" is used in its conventional sense to refer to the end of the hemostasis valve assembly (or component thereof) that is initially inserted into the patient, or that is closer to the patient during use.

Figure 1:
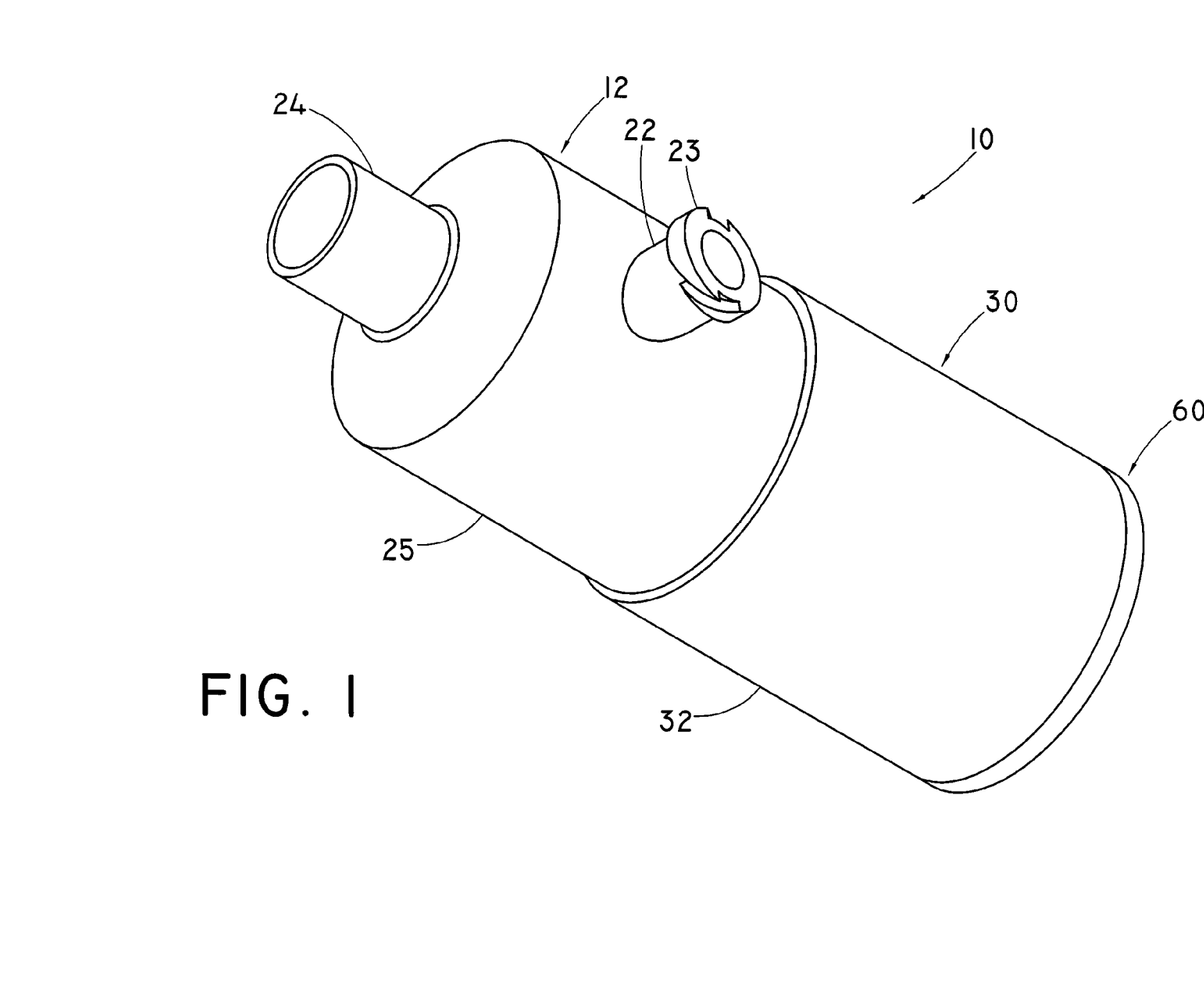
FIG. 1 is a perspective view of a hemostasis valve assembly according to an embodiment of the present invention.
Figure 2:
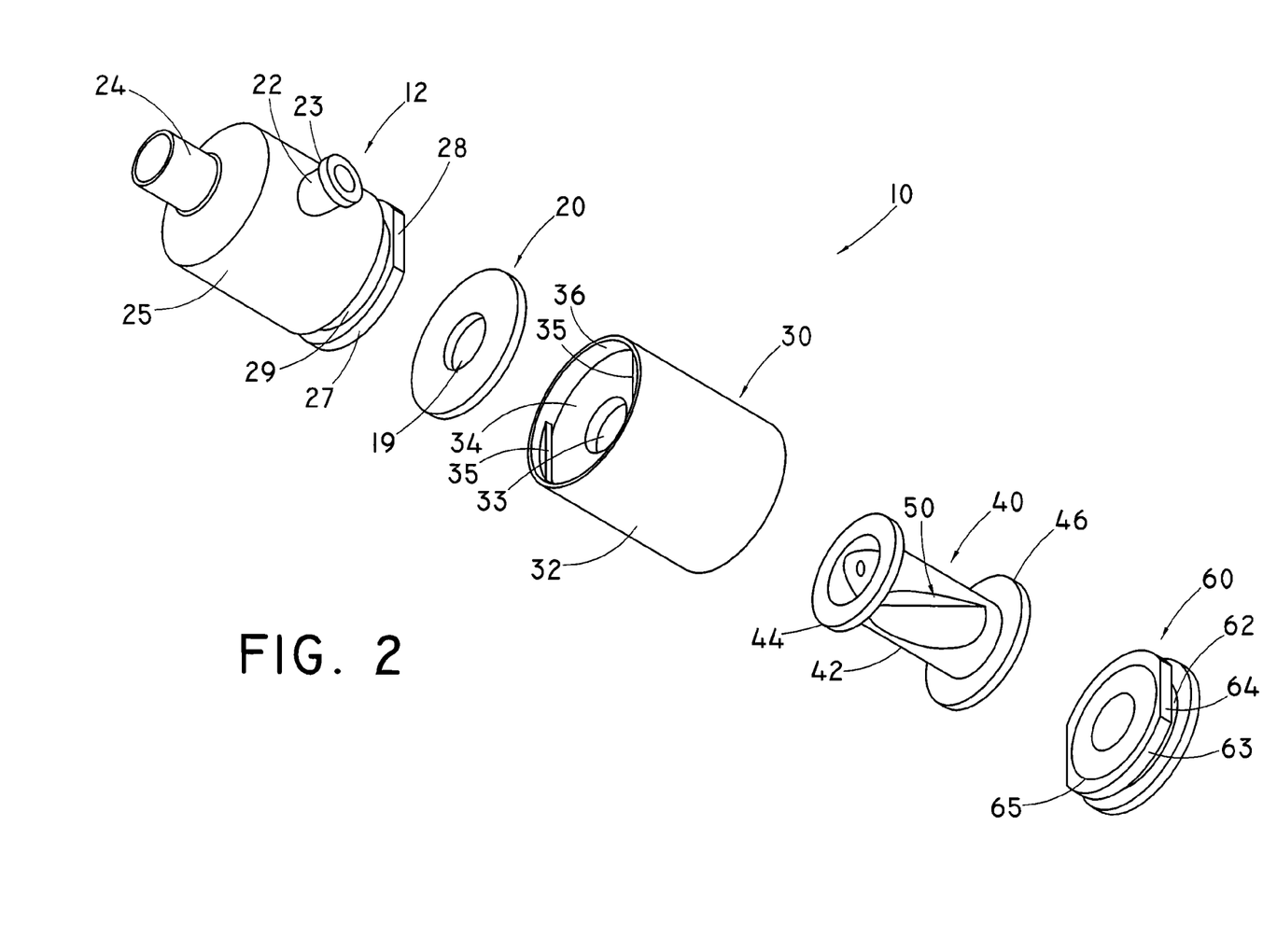
FIG. 2 is an exploded view of the hemostasis valve assembly of FIG. 1.
Figure 3:
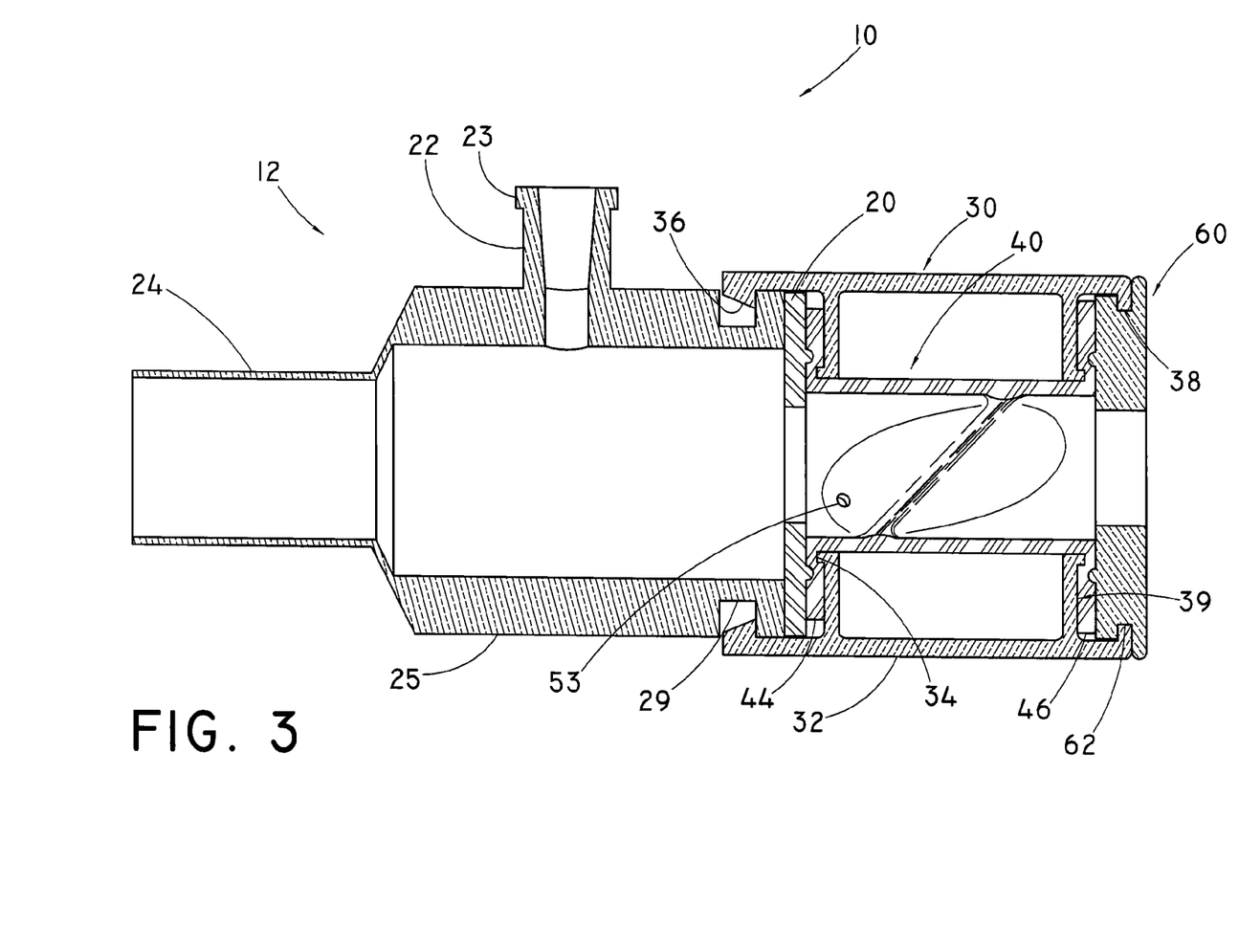
FIG. 3 is a longitudinal sectional view of the valve assembly of FIG. 1.

FIG. 1 is a perspective view of a hemostasis valve assembly 10 according to an embodiment of the present invention. FIG. 2 is an exploded view of hemostasis valve assembly 10 of FIG. 1, and FIG. 3 is a longitudinal sectional view of the hemostasis valve assembly of FIG. 1. Hemostasis valve assembly 10 includes a cannula body 12, a housing 30, and an end cap 60. One or more check valves 20 (only one check valve 20 is shown in the figures) are disposed between cannula body 12 and housing 30. An elastomeric valve sheath 40 is disposed substantially interiorly of housing 30.

The components of valve assembly 10 will now be described in greater detail. In the embodiment shown, cannula body 12 comprises a generally cylindrical body 25 having an interior passageway extending longitudinally therethrough. Cannula body 12 includes a side-arm spout 22 extending transversely therefrom, which spout includes a lip 23 sized and shaped for threaded or like engagement with a tube or other device (not shown) for transmittal or drainage of a fluid or a drug in conventional fashion. The distal end of cannula body 12 comprises a smaller diameter portion 24 for use in engaging valve assembly 10 with a medical device, such as with the proximal end of an introducer sheath (not shown), in conventional fashion. In the non-limiting embodiment shown, a generally annular portion 27 is spaced from cylindrical body 25 at the proximal end of cannula body 12. If desired, annular portion 27 may include two opposing flattened portions 28, only one of which is visible in FIG. 2. Annular portion 27 is spaced from cylindrical body 25 by smaller diameter cylindrical portion 29.

Figures 5, 6:
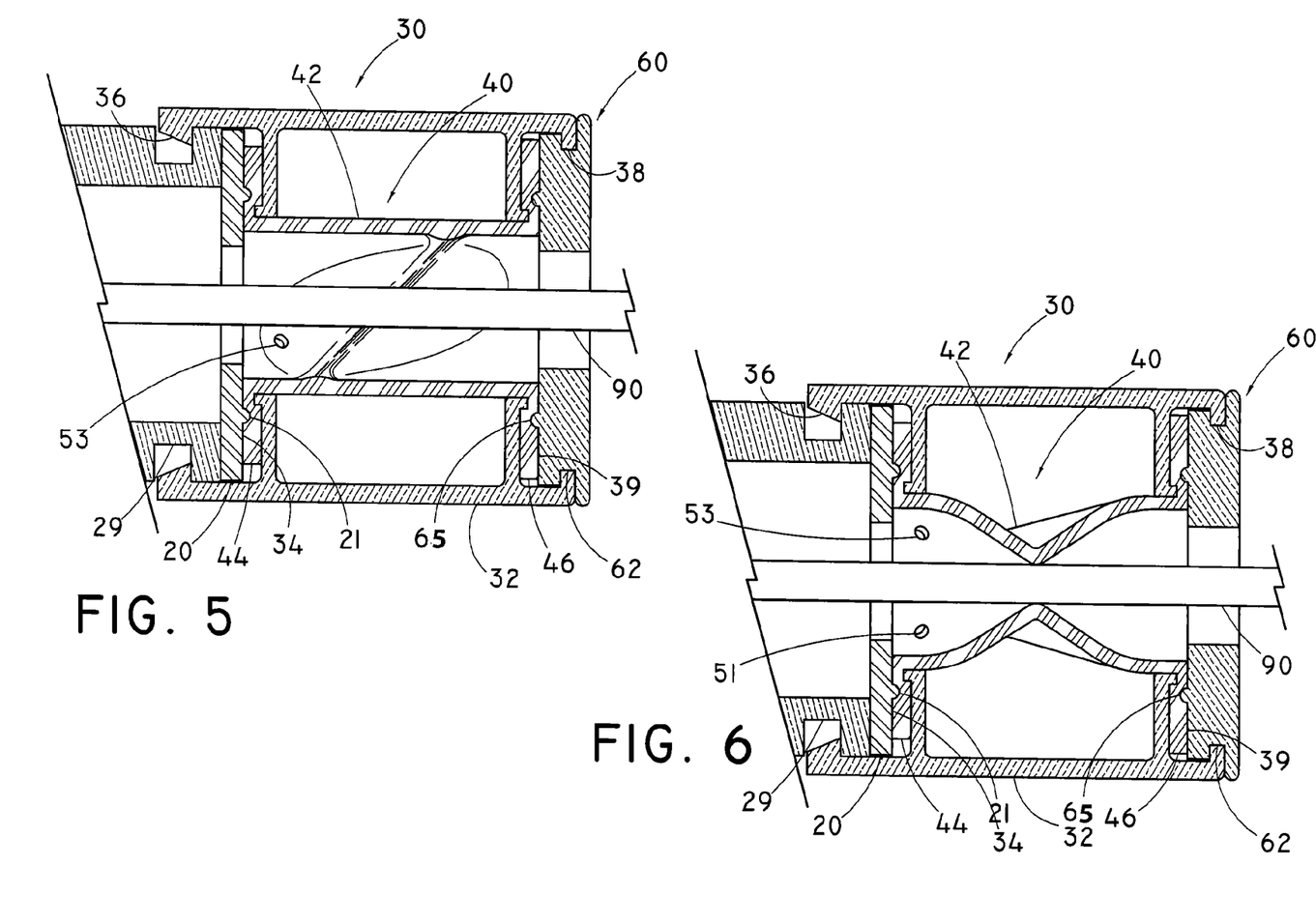
FIG. 5 is a side sectional view of a portion of the valve assembly wherein the valve sheath is oriented substantially as shown in FIG. 4A, and illustrating the presence of an interventional device passing through the valve sheath.
FIG. 6 is another sectional view of the valve assembly and interventional device as shown in FIG. 5, rotated 90° from the orientation of FIG. 5.

Valve disk 20 is preferably a conventional check valve. Such valve disks are commercially available, and may be obtained, for example, from Cook Medical, of Bloomington, Ind., under the name CHECK-FLO® valves. Valve disk 20 is configured in conventional fashion, and may include an aperture 19 to enable passage of an interventional device (not shown) therethrough in well-known fashion. Valve disks are well known in the art. Such disks include various configurations that permit passage of an interventional device therethrough, such as an aperture, a slit, an arrangement of criss-crossed slits, and the like, and may include one or more pressure rings 21 (FIG. 5). Those skilled in the art can readily select an appropriate check valve for use with valve assembly 10. Use of a valve disk 20 in valve assembly 10 is optional. However, it is believed that an enhanced sealing capability is provided around an interventional device when a valve disk is utilized in addition to valve sheath 40.

Housing 30 includes a generally cylindrical main body 32. Main body 32 includes an interior surface 34, 39 at each axial end thereof. Each of surfaces 34, 39 has an aperture extending therethrough, which apertures are aligned to define a passageway 33 that extends through housing 30. As illustrated in FIG. 2, housing 30 may include opposing flattened portions 35 at its distal end that project radially into the inner circumference of housing main body 32. When present, flattened portions 35 are sized and spaced such that when cannula body 12 and housing 30 are engaged as shown in FIG. 1, flattened portions 35 adjoin and rest upon corresponding cannula body flattened portions 28. In this manner, the cannula body 12 and housing 30 are essentially engaged in a manner preventing relative rotation therebetween. Similar flattened portions (not shown) may be provided at the proximal end of housing 30. When present, such proximal flattened portions adjoin and rest upon corresponding flattened portions 64 in end cap 60 (FIG. 2), for preventing relative rotation between housing 30 and end cap 60.

In the embodiment shown, housing 30 also includes a lip 36 at its distal end. Lip 36 is sized to be received in small diameter portion 29 of cannula body 12 to effect engagement between cannula body 12 and the distal end of housing 30, as best shown in FIG. 3. Similarly, housing 30 includes a lip 38 at its proximal end. Lip 38 is sized to be received in small diameter portion 62 of end cap 60, for effecting engagement between the end cap 60 and the proximal end of housing 30. Those skilled in the art will appreciate that there are many other suitable ways in which housing 30 may be engaged with the respective cannula body 12 and end cap 60 other than via corresponding lips 35, 38 as described and shown herein, many of which may be readily substituted for the engagement mechanisms illustrated and described herein.

End cap 60 is best shown in FIG. 2. As shown, end cap 60 may include an annular portion 63 spaced from the distal end of end cap 60 by smaller diameter cylindrical portion 62. As stated above, spaced portion 63 may be provided with flattened portions 64 for engagement with corresponding flattened portions at the proximal end of housing 30. A pressure ring 65 may be provided on the distal surface of end cap 60 for enhancing the seal between end cap 60 and housing 30 in conventional fashion.

Cannula body 12, housing 30, and end cap 60 are preferably formed of a machined or injection molded relatively hard polymeric material, such as acetal, polypropylene, ABS, nylon, PVC, polyethylene or polycarbonate. Preferably, cannula body 12 is formed of a generally transparent polymer that permits viewing therethrough.

Figure 4A:
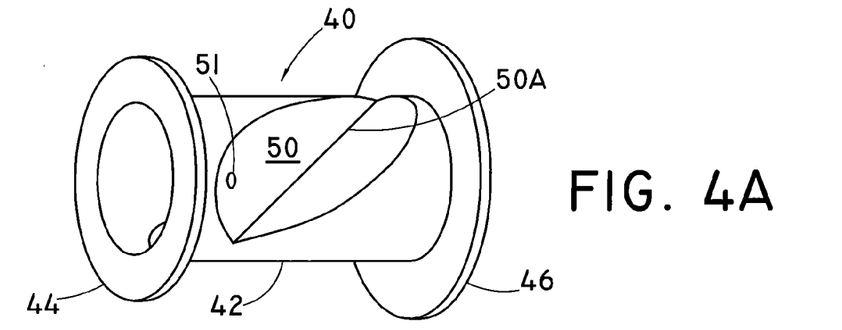
FIG. 4A is a side view of the valve sheath shown in FIG. 2.
Figure 4B:
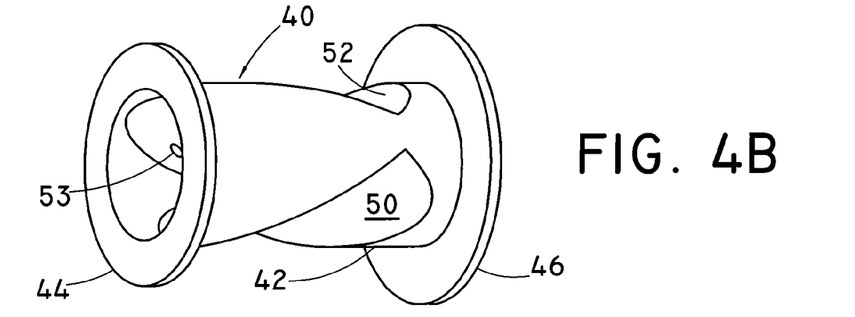
FIG. 4B is a top view of the valve sheath with respect to the orientation of FIG. 4A.
Figure 4C:
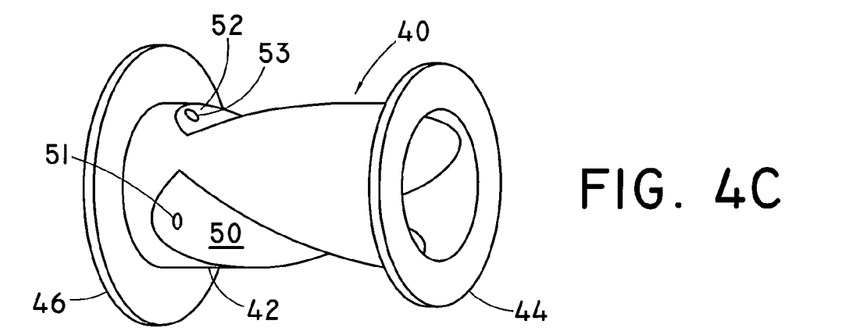
FIG. 4C is a bottom view of the valve sheath with respect to the orientation of FIG. 4A.
Figure 4D:
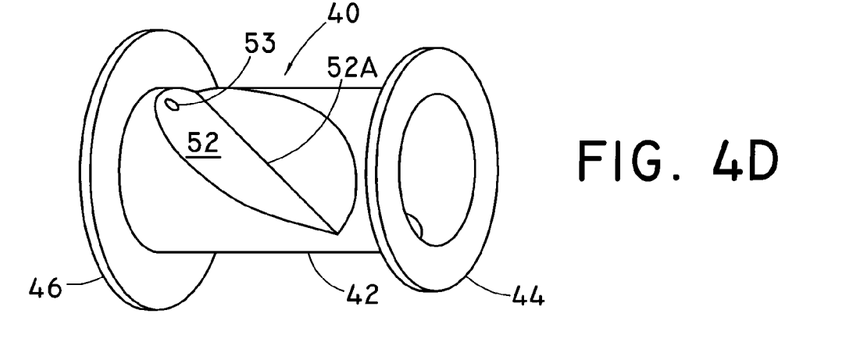
FIG. 4D is a side view of the opposite side of the valve sheath as shown in FIG. 4A.
Figure 4E:
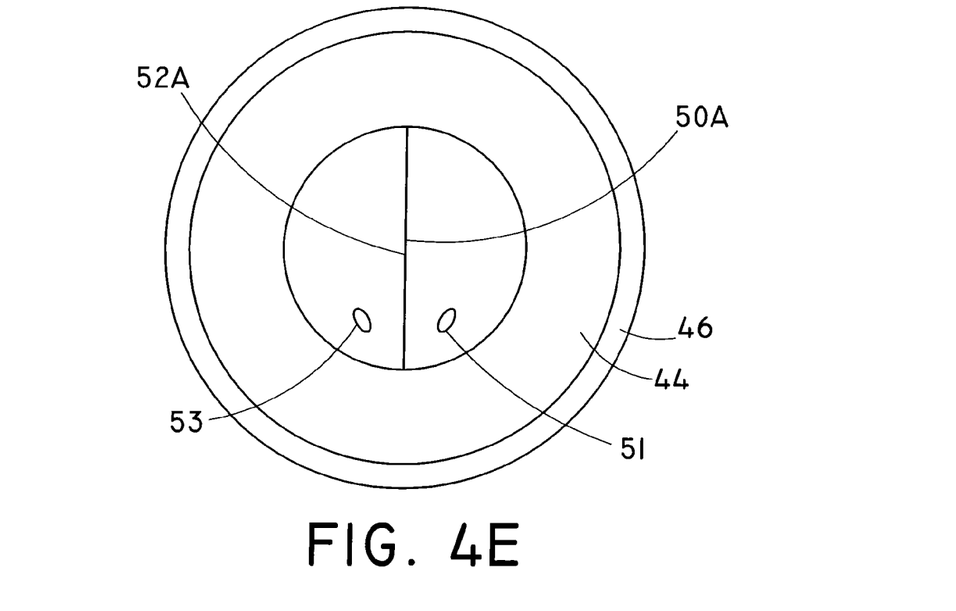
FIG. 4E is a distal end view of the valve sheath as shown in FIG. 4A.
Figure 4F:
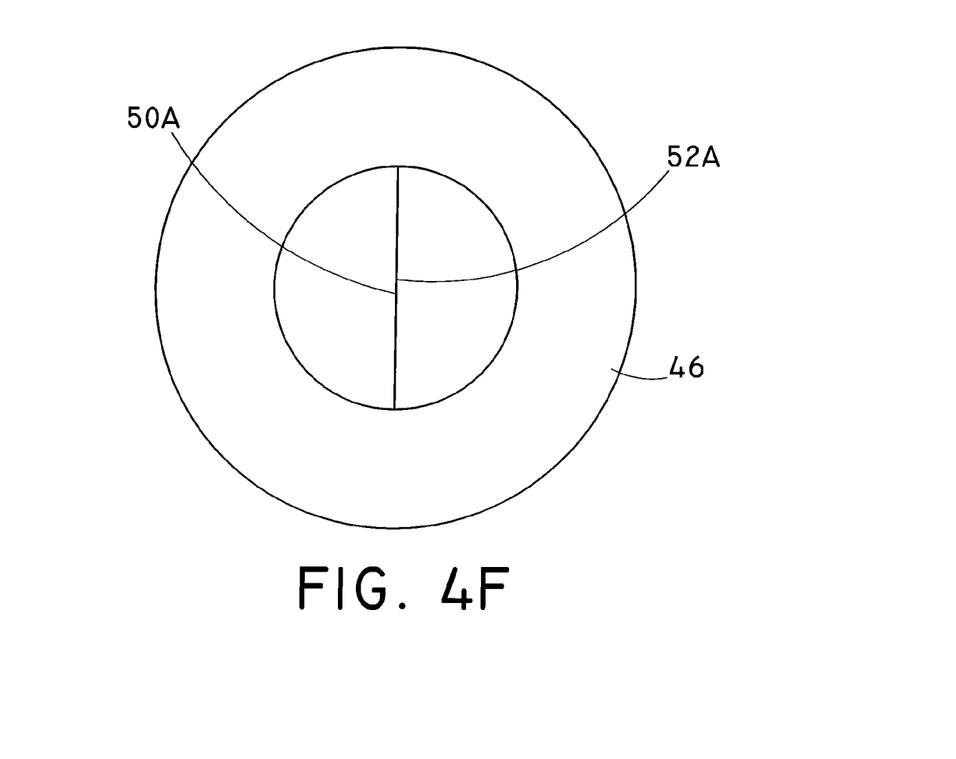
FIG. 4F is a proximal end view of the valve sheath as shown in FIG. 4A.

FIGS. 4A-4F illustrate the features of one embodiment of elastomeric valve sheath 40 in greater detail. FIG. 4A illustrates a side view of the valve sheath shown in FIG. 2. FIG. 4B illustrates a top view of the valve sheath with respect to the orientation of FIG. 4A. FIG. 4C illustrates a bottom view of the valve sheath with respect to the orientation of FIG. 4A. FIG. 4D illustrates a side view of the opposite side of the valve sheath as shown in FIG. 4A. FIGS. 4E and 4F are respective distal (FIG. 4E) and proximal (FIG. 4F) end views of the valve sheath as shown in FIG. 4A.

In the embodiment shown, elastomeric valve sheath 40 comprises a generally cylindrically-shaped valve body 42 as described herein, which valve body is positioned between an annular flange 44 at its distal end and an annular flange 46 at its proximal end. Distal flange 44 is sized and shaped to extend through the aperture in housing surface 34. As shown, e.g., in FIG. 3, distal flange 44 is compressed between the housing surface 34 and annular distal end portion 27 of cannula body 12. In the embodiment shown, optional valve disk 20 is also positioned therebetween. Proximal flange 46 is compressed between the housing surface 39 and the annular distal portion 63 of end cap 60. Each one of flanges 44, 46 includes an aperture sized to permit passage therethrough of an interventional medical device as shown, e.g., in FIGS. 5 and 6. In the non-limiting embodiment shown, proximal flange 46 has a slightly larger outer diameter than distal flange 44. Those skilled in the art will appreciate, however, that the relative diameters of flanges 44, 46 may be varied as desired for a particular application.

Valve body 42 is shaped in a manner to permit passage of the interventional device therethrough, but at the same time, to at least substantially obstruct free passage of a fluid. Cylindrically-shaped body 42 has an elongated void 50, 52 formed along each opposing longitudinal side of the cylindrically-shaped body. In the preferred embodiment shown, voids 50, 52 are generally wedge-shaped, although other configurations may be substituted. Respective voids 50, 52 are configured such that a linear extension is defined along the valve body at an inward terminus of each void. In the embodiment shown in FIGS. 4A-4F, the linear extensions comprise generally diagonal extensions 50A, 52A. Respective diagonal extensions 50A, 52A are aligned to meet along the interior passageway of the valve body. This is best shown in FIGS. 4E and 4F. The two opposing sides of elastomeric valve body 42 are biased inwardly along voids 50, 52 in a manner to essentially pinch the internal passageway shut along diagonal extensions 50A, 52A, thereby inhibiting the flow of fluid therethrough.

If an interventional device is passed through the valve, the portions of the valve inner wall that normally meet to contact one another (as shown in FIGS. 4E, 4F) will be forced apart, allowing passage of the aforementioned device. FIGS. 5 and 6 illustrate longitudinal sectional views of a portion of the hemostasis valve assembly 10 shown herein, illustrating passage through valve sheath 40 of an interventional device, such as introducer sheath 90. FIG. 5 is a side view of assembly 10, wherein valve sheath 40 is oriented in the assembly substantially as shown in FIG. 4A. FIG. 6 is a top view, wherein valve sheath 40 is oriented in the assembly substantially as shown in FIG. 4B. FIG. 6 illustrates the manner in which valve sheath 40 is configured to prevent fluid flow when introducer sheath 90 passes therethrough.

Due to the orientation of the inner sealing surfaces, such as the diagonal orientation shown herein, a device may be passed through the valve from distal to proximal direction, or proximal to distal, with equal ease. Due to the compliant nature of the material used to form the shaped valve body 42, a large diameter device or a small diameter device may generally be passed through the valve with equal ease.

If desired, an aperture 51, 53 may be provided along one or both of the converging walls associated with either, or both, of void spaces 50, 52. Preferably, an aperture 51, 53 is aligned along the length of one side wall associated with each void space 50, 52, as shown in the figures. During use of the valve assembly 10, fluid pressure from the vasculature vents through apertures 51, 53 to the void spaces. This fluid pressure provides additional sealing force to pinch the diagonal extensions together as fluid flows through the valve assembly 10.

As stated, valve sheath 40 is preferably elastomeric. More preferably, the valve sheath is formed of injection molded silicone. A non-limiting list of other suitable materials for use in forming the valve sheath includes isoprene, latex and various rubber or polymeric compositions. For the purposes of the present invention, the durometer of the valve sheath should be less, and preferably considerably less, than the durometer of the body, housing, and end cap. This results in a valve sheath that is softer and more flexible than the remaining structure. If desired, the valve sheath, or preferably, the internal surface only of the valve sheath, can be coated with a lubricious coating, such as parylene, to improve the lubricity of the surface and facilitate the passage of a medical device therethrough. In one preferred embodiment, a distance between flanges 44, 46 is between about 0.5 and 1.0 inch (12.7 and 25.4 mm), and more preferably, about 0.67 inch (17 mm). The length of the valve sheath 40 is preferably equal to or greater than the working diameter of the sheath.

Hemostasis valve assembly 10 may be assembled in the following manner. Initially, the distal end of valve body 42 may be pinched or otherwise compressed, such that distal flange 44 is passed through the apertures of respective housing surfaces 39 and 34. The compression on flange 44 is then relaxed, such that the flange reverts to its normal diameter. In this arrangement, flange 44 is seated on housing surface 34, as shown, e.g., in FIG. 3. Proximal flange 46 is aligned with, and seated on, housing surface 39.

Valve disk 20 may then be loaded onto distal flange 44. Cannula body 12 may then be engaged with housing 30, e.g., by a snap fit wherein housing lip 36 is snapped into small diameter cannula portion 29. In this arrangement, respective cannula body flattened portions 28 and housing flattened portions 35 are aligned such that the flattened portions engage each other, thereby preventing relative rotation between cannula body 12 and housing 30 as described. As a result, valve disk 20 and flange 44 are compressed in the space between cannula body 12 and housing 30 (FIG. 3). Those skilled in the art will appreciate that housing 30 and cannula body 12 need not be engaged by the method described, and other well-known methods of affixation of two parts may be substituted. However, best results are obtained when relative rotation between the two parts is at least substantially prevented.

End cap 60 may be engaged with the proximal end of housing 30 by similar means. In the embodiment shown, end cap 60 is engaged with housing 30 by a snap fit, wherein housing lip 38 is snapped into small diameter end portion 62. In this arrangement, respective end cap and housing flattened portions are aligned, thereby preventing relative rotation between end cap 60 and housing 30. The snap fits described hereinabove can be accomplished in any convenient fashion, such as by use of a small hand press, or by simply snapping the respective portions together by hand pressure. Alternatively, instead of a snap fit, those skilled in the art will appreciate that other engagement means known in the art can be substituted, such as mating screw threads or a friction fit.

Although it is believed that the above-described valve assembly may be constructed to accommodate valve sheaths 40 of virtually all diameters, it is believed that the valve assembly will be particularly effective for use with larger valve sheaths. Large valve sheaths, such as those between about 12 French and 36 French and even larger, are often difficult to seal, and have been prone to the formation of axial gaps in the seals. The closure utilized in the inventive device provides a particularly effective seal when a medical interventional device, such as an introducer sheath, catheter, and the like, of virtually any useable diameter is introduced therein, and also when no catheter is introduced and the lumen of the introducer must be maintained in a closed, substantially leak-proof condition. The valve sheath also has a high resistance to tearing when penetrated by large diameter catheters, and is capable of tolerating repeated catheter insertions and withdrawals without appreciable decrease in performance characteristics of the valve.

As stated above, the presence of a secondary valve source, such as the valve disk(s) 20, is not necessarily required. As a result, in some instances, a separate cannula body 12 may then be omitted, and if desired, any features of the cannula body may be incorporated into a discrete housing 30. Those skilled in the art will appreciate that in this event, housing 30 may be shaped or otherwise configured for attachment to an introducer sheath, and/or may include a side arm spout for transmittal or drainage of a fluid or a drug as described.

Those skilled in the art will appreciate that lubricants and other conventional additives for use with conventional check valves may also be utilized with the check valve(s) 20 as well as with the valve sheath 40 of the present invention. In particular, the use of conventional lubricants between the disks may be desired to inhibit adjacent disks from adhering to each other or to other adjacent structures, and to assist in the smooth movement of the interventional device through the respective valves.

It is therefore intended that the foregoing detailed description be regarded as illustrative rather than limiting, and that it be understood that it is the following claims, including all equivalents, that are intended to define the spirit and scope of this invention.

The invention claimed is:

1. A valve assembly for controlling a flow of fluid, comprising:
   a cannula body having a proximal end and a distal end;
   a housing having a proximal end and a distal end, said housing distal end engaged with said cannula body proximal end, said cannula body and said housing structured and aligned to define a passageway therethrough for passage of an interventional device; and
   a valve sheath having a proximal end and a distal end, said valve sheath disposed at least substantially interiorly of said housing along said passageway, said valve sheath comprising a generally cylindrical valve body having a proximal end, a distal end, and an interior passageway therein for passage of said interventional device in a direction from the proximal end to the distal end of said valve body, and having a pair of elongated voids formed along opposing longitudinal sides of said valve body, said voids configured such that a generally linear extension is defined along the valve body at an inward terminus of each of said voids;
   wherein each of said generally linear extensions includes a proximal end closer to the proximal end of said valve body and a distal end closer to a distal end of said valve body so that each generally linear extension is disposed in a generally diagonal orientation with respect to a longitudinal axis through said valve body, said respective generally linear extensions extending linearly across said interior passageway and being structured and aligned in said valve body to meet along said interior passageway of the valve body in a manner to selectively close said interior passageway, and to yield to permit passage of said interventional device therethrough.

2. The valve assembly of claim 1, wherein at least one of said valve sheath ends comprises a flange, and at least one of said housing ends comprises a valve-receiving surface for said flange.

3. The valve assembly of claim 1, wherein said valve sheath includes a flange at each of said proximal and distal ends, and said housing includes a valve-receiving surface at each of said proximal and distal ends.

4. The valve assembly of claim 3, further comprising an end cap having a proximal end and a distal end, said end cap distal end engaged with said housing proximal end.

5. The valve assembly of claim 4, wherein said distal flange is compressed between said cannula body proximal end and said housing distal end, and said proximal flange is compressed between said end cap distal end and said housing proximal end.

6. The valve assembly of claim 5, further comprising at least one valve disk disposed along said passageway and compressed between said cannula body and said housing generally adjacent said distal flange, said at least one valve disk being conformable to permit passage of said interventional device.

7. The valve assembly of claim 1, wherein each of said voids is generally wedge-shaped, and wherein each of said generally linear extensions is defined at a convergence of first and second inwardly-directed sides of each said void.

8. The valve assembly of claim 7, further comprising an aperture in at least one of said inwardly-directed sides of at least one of said voids.

9. The valve assembly of claim 8, comprising an aperture in one of said inwardly-directed sides of each void.

10. The valve assembly of claim 1, wherein said cannula body and housing are provided with respective flattened portions, said cannula body flattened portions in alignment with said housing flattened portions for preventing relative rotation between said cannula body and said housing.

11. The valve assembly of claim 4, wherein said cannula body and said end cap are provided with respective flattened portions, said cannula body flattened portions in alignment with said end cap flattened portions for preventing relative rotation between said cannula body and said end cap.

12. A valve for use in controlling a flow of fluid, comprising:
a housing, said housing having a proximal end, a distal end, and a passageway extending therethrough;
a valve sheath generally disposed interiorly of said housing at least substantially along said housing passageway, said valve sheath comprising a generally cylindrical valve body having a proximal end, a distal end, and a passageway therein, said valve body having a pair of generally wedge-shaped voids formed along opposing longitudinal sides of said valve body, each of said generally wedge-shaped voids comprising first and second inwardly-directed sides that converge to define a generally linear edge, each of said edges including a proximal end closer to the proximal end of said valve body and a distal end closer to a distal end of said valve body so that each edge is disposed in a generally diagonal orientation with respect to a longitudinal axis through said valve body, said respective linear edges extending linearly across said interior passageway and being structured and aligned in said valve body to meet along said valve body passageway in a manner to selectively close said valve sheath interior passageway and to yield to permit passage of an interventional device therethrough.

13. The valve of claim 12, further comprising a flange at each of said proximal and distal ends of said valve body, said housing including a valve-receiving surface at each of said proximal and distal ends, each said surface configured and arranged to receive one of said flanges.

14. The valve of claim 12, further comprising an aperture through one of said inwardly-directed converging sides of each of said wedge-shaped voids.

* * * * *